United States Patent
Archer et al.

[11] Patent Number: 5,993,774
[45] Date of Patent: *Nov. 30, 1999

[54] METAL-OXIME CHELATES FOR USE AS RADIOPHARMACEUTICAL AGENTS

[75] Inventors: Colin Mill Archer; Lewis Reuben Canning; Harjit Kaur Gill, all of Chesham; Anthony Leonard Mark Riley, Marlow, all of United Kingdom

[73] Assignee: Amersham International plc, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/411,791
[22] PCT Filed: Oct. 8, 1993
[86] PCT No.: PCT/GB93/02088
 § 371 Date: May 9, 1995
 § 102(e) Date: May 9, 1995
[87] PCT Pub. No.: WO94/08949
 PCT Pub. Date: Apr. 28, 1994

[30] Foreign Application Priority Data

Oct. 8, 1992 [EP] European Pat. Off. ............. 92309194

[51] Int. Cl.$^6$ ............. A61K 51/00; A61M 36/14
[52] U.S. Cl. ............. 424/1.65; 424/1.11; 424/1.69; 534/14; 534/10
[58] Field of Search ............. 534/10, 14, 16; 556/35, 37; 424/1.65, 1.11, 1.69; 544/1

[56] References Cited

U.S. PATENT DOCUMENTS

| | | | |
|---|---|---|---|
| 4,615,876 | 10/1986 | Troutner et al. | 424/1.1 |
| 4,789,736 | 12/1988 | Canning et al. | 534/14 |
| 4,818,813 | 4/1989 | Nowotnik et al. | 534/14 |
| 5,116,598 | 5/1992 | Nosco | 424/1.1 |
| 5,310,536 | 5/1994 | Srinivasan | 424/1.65 |
| 5,387,692 | 2/1995 | Riley et al. | 548/313.7 |
| 5,589,576 | 12/1996 | Archer et al. | 534/14 |
| 5,608,110 | 3/1997 | Ramalingam et al. | 564/253 |
| 5,645,814 | 7/1997 | Woulfe et al. | 424/1.65 |
| 5,651,954 | 7/1997 | Nowotnik et al. | 424/1.65 |
| 5,663,307 | 9/1997 | Nowotnik et al. | 534/10 |

FOREIGN PATENT DOCUMENTS 502595  3/1992  European Pat. Off. .

OTHER PUBLICATIONS

Moody et al., *J. Chem. Soc.*, Perkins Trans. 1(1), pp. 18–24, 1972.
Lan et al., *J. Am. Chem. Soc.*, 100(6), pp. 1857–1865, 1978.

*Primary Examiner*—Jose' G. Dees
*Assistant Examiner*—Dameron Jones
*Attorney, Agent, or Firm*—Wenderoth, Lind & Ponack, L.L.P.

[57] ABSTRACT

Novel metal chelating compounds, and radiometal, e.g., technetium-99m complexes thereof. The compounds can be used to radiolabel small biologically active species with minimal effect on their biodistribution and activity. The compounds have formula (a) or (b):

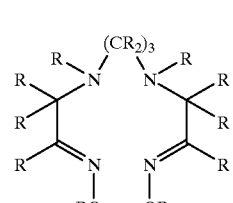

(a)

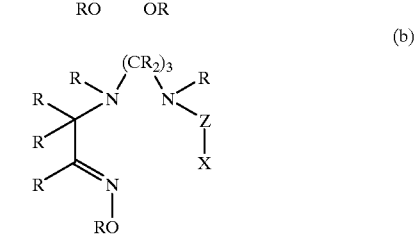

(b)

where Z is $(CR_2)_n$ or $(CR)_n$, n is 2 or 3, X is a ligand comprising S, N or O, each R is H or C1–C20 substituted or unsubstituted hydrocarbon group, provided that 1–3 $CR_2$ groups represent a CO (amide) moiety, and provided that 1–3 R may each comprise a targeting group and/or a protein reactive functionality.

10 Claims, 6 Drawing Sheets

(Compound XIII)

FIG. 6

(Compound XIV)

METAL-OXIME CHELATES FOR USE AS RADIOPHARMACEUTICAL AGENTS

This application is a 371 of PCT/GB93/02088 filed Oct. 8, 1993.

This invention concerns metal-chelating compounds which are intended mainly for radio-pharmaceutical use. The compounds comprise a metal-chelating moiety, and either a biological targeting group or a protein reactive functionality. Targeting groups of particular interest are bioreductive groups, which may provide compounds useful as hypoxia agents. Prior art relating to ligand systems.

The tetradentate diaminedioxime ligands shown, and their metal complexes, were first described by R K Murmann et al.

n = 2, 3

J Am Chem Soc. 84, 1349 (1962)
Inorg Chem, 6 2043 (1967)

EP 0123504 B describes the technetium complexes of such ligands, and substituted versions thereof and their use as radiopharmaceuticals.

EP 0179608 B describes the unsymmetrical diaminedioxime ligands shown and their technetium complexes:

where $R_{1-9}$ are independently H or $C_{1-4}$ alkyl,

EP 0380016 A describes the d1 isomers of the following ligands, and their technetium complexes:

where R is bivalent radical completing a 4–5 membered ring.

U.S. Pat. No. 5,116,598 describes technetium complexes of tetradentate $N_4$ ligands bearing at least one pendant $CO_2H$ group.

$R_4$ and $R_5$ or $R_8$ and $R_9$ may be combined to form an oxygen atom. Hydroxylamine (C—N—O) ligands are shown rather than oximes (C=N—O). The text gives no further clarification. No examples are given.

PRIOR ART RELATING TO HYPOXIA AGENTS

It is known that certain molecules, known as bioreductive moieties, are capable of diffusing into and becoming immobilised in hypoxic cells. (See Mason, P. "Free Radicals in Biology" Academic Press 1982). Thus for example nitroimidazoles, and in particular, misonidazole (3-methoxy-1-(2-nitromidazol-1-yl)propan-2-ol) are used against anaerobic bacteria and as radiosensitising agents for hypoxic tumours. It is known that anaerobic metabolism leads to free radical formation and subsequent covalent binding of the nitroimidazole (or degradation product) within the hypoxic cell. In the presence of oxygen (aerobic cells), re-oxidation of the free radicals occurs continuously in a 'futile cycle'. Thus it is only under anaerobic conditions that the free radicals can exist long enough for combination with cellular components to occur, i.e. trapping in hypoxic tumours or in ischaemic, but viable myocardium.

Chelated metal atoms may, in certain circumstances, be incorporated into bioreductive molecules without destroying the ability of the bioreductive molecules to discriminate between oxic and hypoxic cells. Radioactive metals can be used.

EPA 502595 claims compounds of the following general formula where B may be a substituted nitrosomethyl group, A is a targeting or functional group and $R^1$ to $R^5$ are as defined. These compounds are said to form complexes with radioactive metal ions which are suitable for diagnosis and tumor therapy. No compound is described in which B is nitrosomethyl or substituted nitrosomethyl.

EPA 417870 describes similar compounds for similar uses, but in which the two CO amide groups are replaced by $CH_2$ groups.

WO 91/18008 describes $^{99m}$Tc-cyciopentadienyl carbonyl complexes of general formula (I) in which —X—R can have various meanings including (I)

U.S. Pat. No. 4,193,979 describes sodium 3-(((2-(2-methyl-5-nitro-1H-imidazole-1-yl)ethyl)-amino)carbonyl)-2-pyridine-carboxylic and related compounds which are labelled with $^{99m}$Tc. The agents are said to be useful as gall bladder and liver imaging agents. No 2-nitroimidazole derivatives are described.

EP 0 441 491 A1 claims boronic acid adducts of $^{99m}$Tc dioxime or rhenium dioxime complexes which are linked through alkyl or alkenyl linkers to a biochemically reactive group. The said biochemically reactive group may be a hypoxia-mediated nitroheterocyclic group, in which case, the agents are said to provide a method for diagnostic imaging or radiotherapy of hypoxic tissue.

In KE Linder et al J Nucl Med 33, 5, (1992) Proc. 39th Annual Meeting, p865 and p919 (Bristol-Myers Squibb), a Tc-PAO-nitroimidazole is described which localizes in hypoxic tissue (LAD occluded New Zealand rabbit heart). The structure of the compound was given as:

THE INVENTION

In one aspect this invention provides, subject to a disclaimer (see below), metal-chelating compounds of the formula $Z^1$ = R or a thiol protecting group, R = same or different, H, $C_{1-20}$ hydrocarbon which may be: - alkyl, alkoxy, alkoxyalkyl, primary secondary or tertiary amide, primary secondary or tertiary amine, carboxylic acid, hydroxyalkyl, aryl, or 1 to 3 of the $CR_2$ groups adjacent a N atom may represent a CO (amide) moiety, or two R's of any $CR_2$ group and/or two or more separate $CR_2$ groups may be combined to form a C3–C6 cycloalkyl, aryl, spiropiperidinyl or other heterocyclic ring, provided that in the compounds of formula a) at least one $CR_2$ group adjacent a N atom represents a CO (amide) moiety, and provided that one to three R may each optionally comprise a targeting group and/or a protein reactive functionality.

In another aspect, the invention provides radiometal complexes of the compounds defined.

The thiol protecting group $Z^1$ may be trityl, benzoyl, tetrahydropyran, benzyl, or the corresponding disulphide dimer or others well known in the art.

The ring system of a) is related to the ethylene diaminedioxime and propylene diaminedioxime ligands described by R K Murmann et al. A feature of this invention is that from 1 to 3 of the $CR_2$ groups adjacent a N atom represent a CO (amide) moiety. The significance of this feature is discussed below. In the case of the preferred propylene diaminedioxime ligands, there are four $CR_2$ groups adjacent N atoms, of which 1 to 3 represent CO (amide) moieties. The following ligand systems are particularly envisaged So far as the ligand systems b) are concerned, there are generally three to five $CR_2$ groups adjacent a N atom, of which 1 to 3 may optionally (and preferably do) represent a CO (amide) moiety. Examples of such ligand systems b) are shown below, with the positions which can optionally be occupied by a CO (amide) group being marked with a star.

The invention envisages that these ligand systems can be used to radiolabel biologically active species, especially small molecules (molecular weight less than a thousand, with minimal effect on their biodistribution and activity. Thus in the compounds of the invention, at least one group R, and preferably one or two groups R, may comprise a targeting group and/or a protein reactive functionality. Examples of targeting groups are:

bioreductive molecules (e.g. 2-nitroimidazole)—for diagnosis/therapy of hypoxia and hypoxic tumors biologically active peptides—e.g. somatostatin analogues for cancer diagnosis and therapy, or cell adhesion peptides containing the RGD sequence for thrombus imaging receptor ligands—e.g. dopamine ligands for brain receptor imaging, steroids for estrogen receptor imaging metabolic markers—glucose or fatty acids to track myocardial and/or brain metabolism, diacylglycerols proteins and antibodies.

Protein reactive functionalities are well known and include for example isothiocyanate, haloacetamide, active ester, thioester, amino, mercapto, hydrazino, carboxyl, alkenyl or alkynyl, oxiranyl, fluorinated phenoxycarbonyl, optionally substituted succinimidoxycarbonyl, aminophenyl, isothiocyanatophenyl, and others.

The (or each) group R, comprising a targeting group and/or a protein reactive functionality, is preferably attached to a carbon atom adjacent a nitrogen atom.

In these compounds, the bioreductive moiety may be any which has the ability to cause the agent to become trapped in hypoxic cells, for example those discussed by P. Mason in "Free Radicals in Biology", Academic Press, 1982, including quinones and aromatic nitro-compounds. Preferred are benzotriazine-di-n-oxides, triazoles, nitroacridines, nitrofurans, nitroimidazoles including particularly 2-nitroimidazole, and their substituted analogues such as misonidazole. Alkyl, acyl, chloro-, bromo-, hydroxyalkyl, alkoxyalkyl, aminoalkyl, and other substituents may improve the properties of these bioreductive molecules. Other references to bioreductive molecules include: J. H. Tocher et al., Free Rad. Res. Comms., Vol 10, Nos. 4–5, pp 295–302, 1990; Y. Nagao et al., Tetrahedron, Vol. 46, No. 9, pp 3211–3232, 1990; and W. A. Denny et al., J. Med. Chem., 1990, 33, 1288–1295.

These compounds may have the formula Q-A-L or $(Q-A)_2$-L where Q is the targeting group and/or protein reactive functionality A is a linking group, and L is the metal-chelating moiety of formula a) or b).

In these compounds, the metal chelating moiety L is joined to the targeting group Q by means of a linking group A. Group A preferably comprises a chain from 1 to 12 atoms long, in which hetero atoms such as S, N and O are possible, as also are amide and ester linkages. The linking group A should not be so charged or so polar as to prevent diffusion of a complex (of the compound with a radiometal) through cell walls.

The compounds of this invention may be made by known chemical reactions from known starting materials. Preparative details are given in the experimental section below and in the reaction schemes 1 to 5.

The invention also includes radiometal complexes of the compounds described.

The term radiometal is used herein to describe the metal species which may be present in a variety of oxidation states, or even associated with O, OH, Cl, etc., depending on its chemistry. Preferred radiometals include $^{99m}$Tc, $^{186}$Re, $^{188}$Re, $^{67}$Cu and $^{107}$Ag. The radiometal complexes are readily made by allowing the mixed reagents to stand at room temperature. For example, technetium $^{99m}$ complexes may be made by mixing a solution of the metal chelating compound with technetium generator eluate, in the presence of a reducing agent, and allowing the mixture to stand at ambient temperature for some minutes or hours.

The present invention thus provides a range of ligand systems which can be tailored to a given radiopharmaceutical application. Thus substitution of one or more amide groups into the donor set of tetradentate diaminedioxime ligands provides a means of controlling the charge, size, molecular weight, stability and lipophilicity of the corresponding metal complexes.

The previously known diaminedioxime ligands are limited in that the donor set is designed to give neutral, lipophilic technetium complexes. A further restriction is that one or more alkyl substituents a to the amine nitrogen are essential in order to confer complex stability. The effect of these alkyl substituents is clearly to increase both complex size and lipophilicity. The lipophilicity of such complexes can only be reduced by increasing size i.e. by adding polar substituents (e.g. carboxyl, amine or alcohol).

We have shown that, by changing the donor set, a range of charged or neutral technetium complexes results. Thus, for example, it is possible to maintain or increase complex stability whilst reducing both size and lipophilicity by replacing an $NC(CH_3)_2$ moiety with NC=O.

It is also possible to replace $NCH_2$ with NC=O with minimal effect on size.

It is anticipated that the more compact radiometal complexes will be useful in radiolabelling biologically active molecules with minimal effect on their activity and/or biodistribution. Choice of a suitable complex type from a range of varying charge, size, lipophilicity etc. permits control over the degree of plasma protein binding, cell permeation ability, clearance route etc.—all important parameters in radiopharmaceutical design.

We have further shown that the hydrogen bond formed between the two terminal oxime groups in metal complexes of the above diaminedioximes is not essential for complex stability. Thus unsymmetrical tetradentate. ligands with only a single oxime group as in structure (b) can still form stable radiometal complexes useful as radio-pharmaceuticals.

When a bioreductive moiety is present, the complexes of this invention are useful as hypoxia agents.

In vitro, the agent is capable of diffusing freely into oxic or hypoxic cells, but is preferentially trapped in hypoxic cells. In vivo where the agent is transported by the blood to hypoxic regions it diffuses through the cell walls. Once within the hypoxic cells it is a substrate for nitroreductases producing free radicals which, in the absence of $O_2$, become trapped, e.g. as a result of covalent bonding, within the cell. For these purposes, the agent has certain characteristics:

The agent as a whole is capable of diffusing into cells, for which purpose its partition coefficient is important. If the agent is too hydrophilic, it will not diffuse through cell walls. If it is too hydrophobic, it may be completely water-insoluble. The hydrophilic/lipophilic balance can quite readily be adjusted, e.g. by addition of hydrophilic or hydrophobic groups to the chelating moiety L or to the linking group A or to the bioreductive moiety Q, provided that the molecule should not be so charged or so polar as to prevent its diffusion through the cell walls.

Once in hypoxic cells, the agent is capable of being immobilised. For this purpose, the nitro or other bioreductive moiety should not be hindered by the chelating moiety.

The chelating moiety strongly binds the metal, and does not significantly release it in solution or in the bloodstream. Thus, the metal is introduced and becomes immobilised within the hypoxic cells.

Our agents have the advantage that they enter cells by passive diffusion rather than by active transport. Compounds which enter cells by active transport are likely to have their properties impaired by substitution with metal chelating moieties.

Our agents are expected to be useful for myocardial viability assessment, perhaps in conjunction with current myocardial perfusion imaging techniques; of particular interest in this connection are agents in which at least one group R is C6–C20 carboxyl. Our agents are also expected to be useful for cerebral viability assessment. Because tumours are often hypoxic, the agents are expected to be useful for both diagnosis and treatment of hypoxic tumours.

EXAMPLES 3-amino-3-methylbutan-2-one monoxime[1] and 3-(3-aminopropyl)amino-3-methyl-2-butanone oxime[2] were prepared according to published methods.
1. R K Murmann, J Am Chem Soc, 79, 521 (1957).
2. EP 0179608 B1.

Synthesis of 2-(tBoc amino)-N-[3-(2-hydroxyimino-1,1-dimethyl)propylamino]propylacetamide (Compound I)

To a solution of 3-(3-aminopropyl)-amino-3-methyl-2-butanone oxime (0.5 g; 2.9 mmol) in acetonitrile (25 ml), stirred under a dry dinitrogen atmosphere, was added a solution of N-tBoc-glycine-N-hydroxysuccinimide ester (0.79 g; 2.9 mmol) in acetonitrile (25 ml). The reaction mixture was stirred for ca 18 h. and then the solvent was removed in vacuo. The residue was redissolved in 50:50 acetonitrile/water (10 ml) and the product, Compound I (180 mg; 19%), was isolated by preparative HPLC purification.

HPLC Purification
Column: $C_{18}$-PRP-1 (Preparative Reverse Phase)
Solvents: A=2% aq. $NH_3$, B=MeCN-System: Isocratic 30% B
Flow Rate: 2.5 ml/min.
U.V detector: λ=210 nm
Retention time of product: 9.6 min.
Analysis:

| | |
|---|---|
| $^1$H NMR : | (CD$_3$OD) |
| δ (ppm) : | 1.25 (s; 6H; —CH$_3$), 1.42 (s; 9H; —C(CH$_3$)$_3$), |
| | 1.60 (t; 2H; —CH$_2$), 1.85 (s; 3H; —CH$_3$—C=N—O), |
| | 2.44 (t; 2H; —CH$_2$—N), 3.24 (t; 2H; —CH$_2$—N—C=O), |
| | 3.68 (s; 2H; —CH$_2$—C=O) |
| $^{13}$C NMR : | (CD$_3$OD) |
| δ (ppm) : | 10.4 (s), 26.5 (s), 29.5 (s), 31.6 (s), |
| | 39.3 (s), 42.4 (s), 45.4 (s), 59.3 (s), |
| | 81.5 (s), 159.0 (s), 162.3 (s), 173.2 (s) |

Synthesis of 2-amino-N-[3-(2-hydroxyimino-1,1-dimethyl)propylamino]propylacetamide (Compound II)

Compound I (0.8 g; 2.42 mmol) was dissolved in hydrochloric acid (3M; 20 ml) and the mixture was stirred at RT for ca 1 h. After stirring, the crude reaction solution was basified with potassium hydroxide (2M) to ca pH10 prior to HPLC purification, from which pure fractions of Compound II were collected. The fractions were bulked together and the solvent was removed in vacuo isolating the product as a clear oil (0.40 g; 72%).

HPLC Purification
Column: $C_{18}$-PRP-1 (Preparative Reverse Phase)
Solvents: A=2% aq. $NH_3$, B=MeCN-System: Gradient
Flow Rate: 2.5 ml/min.
U.V detector: λ=210 nm
Gradient Profile:

| Time | % B |
|---|---|
| 0 | 5 |
| 5 | 80 |
| 10 | 80 |
| 12 | 5 |
| 15 | 5 |

Retention time of product: 10.0 min.
Analysis:

| | |
|---|---|
| $^1$H NMR : | (CD$_3$OD) |
| δ(ppm) : | 1.25 (s; 6H; —CH$_3$), 1.70 (t; 2H; —CH$_2$), |
| | 1.85 (s; 3H; —CH$_3$—C=N—O), 2.50 (t; 2H; —CH$_2$—N), |
| | 3.2–3.4 (m + s ; 2H + 2H – overlapping) |

Synthesis of N-[3-(2-hydroxyimino-1,1-dimethyl)propylamino)propyl-2-mercaptoacetamide (Compound IV)

3-(3-aminopropyl)-amino-3-methyl-2-butanone oxime (0.25 g; 1.44 mmol) was dissolved in ethanol (10 ml) and stirred at RT under a dry dinitrogen atmosphere. To this solution, ethylmercaptoacetate (0.119 g; 0.21 ml) was added dropwise with care. After addition was complete the reaction mixture was stirred for ca 24 h., whence a yellow precipitate formed.

The mother liquor was decanted off and the precipitate was suspended in absolute ethanol (5 ml) prior to filtration in air. The solid product was washed with aliquots of ethanol (3×1 ml) and dried in vacuo, yielding Compound IV as a yellow powder, (0.11 g; 31%).
Analysis:

| $^1$H NMR : | (DMSO-d$_6$) |
|---|---|
| δ (ppm) : | 1.30 (s; 6H; —CH$_3$), 1.82 (t; 2H; —CH$_2$), 1.95 (s, 3H; CH$_3$—C=N—O), 2.5 (signal masked by solvent), 3.52 (m; 2H; —CH$_2$—N), 3.80 (t; 2H; O=C—CH$_2$—S), 9.2 (t; 1H; —SH), 10.65 (d; 2H; —NH) |

Synthesis of 3-amino-N-[(2-hydroxyimino-1,1-dimethyl) propyl]propanamide (Compound V)

A mixture of benzoyloxycarbonyl-β-ala-N-hydroxysuccinimide ester (6.4 g; 20 mmol) and 3-amino-3-methylbutan-2-one-2-monoxime (2.32 g; 20 mmol) in dimethylformamide (50 ml) was stirred at RT, under a dry dinitrogen atmosphere, for ca 1 h. The solvent was then removed in vacuo and a mixture of water (50 ml) and diethylether (50 ml) was added to the residue. The insoluble component was filtered off in air and dried in vacuo. Recrystallisation of a solution of the product in dichloromethane\40–60 petrol ether at −4° C. yielded clear crystals of 7-amino-4-aza- 7-benzoyloxycarbonyl-3,3-dimethylheptane-2,5-dione-2-monoxime, (3.96 g; 62%).

To a solution of 7-amino-4-aza-7-benzoyloxycarbonyl-3,3-dimethylheptane-2,5-dione-2-monoxime (3.95 g; 12.3 mmol) in warm ethanol (100 ml, 40° C.), stirred under a dry dinitrogen atmosphere, was added a palladium/carbon catalyst (400 mg). Hydrogen gas was bubbled through the reaction solution for ca 2 h. and then the solution was filtered off. The solvent was removed under reduced pressure, yielding Compound V as a white crystalline solid, (1.32 g; 57%).
Analysis:

| m.p. : | 113–116° C. |
|---|---|
| $^1$H NMR : | (CD$_3$OD) |
| δ (ppm) : | 1.40 (s; 6H; —CH3), 1.78 (s; 3H; —CH$_3$), 2.30 (t, 2H; CH$_2$—CH$_2$—NH$_2$), 2.84 (t; 2H; O=C—CH$_2$—CH$_2$). |
| $^{13}$C NMR : | (CD$_3$OD) |
| δ (ppm) : | 10.58 (s), 26.76 (s), 39.81 (s), 40.36 (s), 58.21 (s), 162.08 (d), 174.40 (s). |

Synthesis of 10-(tBoc amino)-4,8-diaza-3,3-dimethyldecan-2,5,9-trione-2-monoxime (Compound VI)

To a stirred suspension of Compound V (0.15 g; 0.8 mmol) in dry acetonitrile (25 ml), maintained under a dry dinitrogen atmosphere, was added a solution of t-Boc-glycine-N-hydroxysuccinimde ester (0.22 g; 0.8 mmol) in dry acetonitrile (10 ml) over a period of ca 2 minutes. The reaction mixture was stirred until the solution became clear, (ca 3 h.), indicating that the reaction had gone to completion. The solvent was removed in vacuo giving a paste which was then redissolved in dilute sodium hydroxide (10 ml; pH10) and extracted into dichloromethane (3×20 ml). The extracts were separated, bulked together, dried over MgSO$_4$, filtered and finally the solvent was removed under reduced pressure, yielding Compound VI (60 mg; 21%) as a white solid.
Analysis:

| $^1$H NMR : | (CD$_3$OD) |
|---|---|
| δ (ppm) : | 1.40 (s; 6H; —CH$_3$), 1.45 (s; 9H; —C(CH$_3$)$_3$), 1.75 (s; 3H; CH$_3$—C=N—O), 2.38 (t, 2H; —CH$_2$), 3.42 (t; 2H; CH$_2$—CH$_2$—C=O), 3.65 (s; 2H; O=C—CH$_2$—N) |

Synthesis of 10-amino-4,8-diaza-3,3-dimethyl-decan-2,5,9-trione-2-monoxime (Compound VII)

Compound VI (60 mg; 0.17 mmol) was dissolved in hydrochloric acid (3M; 20 ml) and the mixture was stirred at RT for ca 1 h. The crude reaction solution was then basified with potassium hydroxide (2M) to ca pH10 prior to HPLC purification, from which fractions of the desired product were collected. The fractions were bulked together and the solvent was removed in vacuo isolating the product, Compound VII as a clear oil (40 mg; 88%).
HPLC Purification
Column: C$_{18}$-PRP-1 (Preparative Reverse Phase)
Solvents: A=2% aq.NH$_3$, B=MeCN-System: Gradient
Flow Rate: 2.5 ml/min.
U.V detector: λ=210 nm
Gradient Profile:

| Time | % B |
|---|---|
| 0 | 5 |
| 5 | 80 |
| 10 | 80 |
| 12 | 5 |
| 15 | 5 |

Retention time of product: 9.8 min.
Analysis:

| $^1$H NMR : | (CD$_3$OD) |
|---|---|
| δ (ppm): | 1.30 (s; 6H; —CH$_3$), 2.1 (s; 3H; CH$_3$—C=N—O), 2.40 (t, 2H; CH$_2$—CH$_2$—N), 3.20 (s; 2H; O=C—CH$_2$—N), 3.45 (t; 2H; CH$_2$—CH$_2$—C=O). |

Synthesis of 3-amino-N,N'-bis-[2-hydroxyimino-1,1-dimethyl)propyl]propanamide (Compound VIII)

To a stirred mixture of Compound V (0.5 g; 2.88 mmol) and NaHCO$_3$ (1 g; 12 mmol) in acetonitrile (15 ml) was added a solution of 3-chloro-3-methyl-2-nitrosobutane (0.43 g; 3.2 mmol) in acetonitrile (20 ml) over a period of ca 1 h. After addition, the reaction mixture was stirred for ca 18 h. at RT, and then the solvent was removed under reduced pressure. The residue obtained was redissolved in the minimum volume of dil. HCl (2M) to produce a clear solution at pH=5. Any undesired organic material was extracted into diethylether (3×30 ml), the phases were separated, and the aqueous phase retained. The pH of the aqueous phase was re-adjusted to pH=10 using dil NaOH (0.1M), and the solution was fridge-stored for ca 72 h., whence a white flocculent solid formed.

The product was filtered off in air to yield Compound VIII (104 mg; 13%) as a white powder.
Analysis:

| m.p. : | 165–168° C. |
|---|---|
| $^1$H NMR : | (CD$_3$OD) |
| δ (ppm) : | 1.22 (s; 6H; —CH$_3$), 1.40 (s; 6H; —CH$_3$), 1.75 (s; 3H; —CH$_3$—C=N—O), 1.80 (s; 3H; —CH$_3$—C=N—O), 2.30 (t; 2H; N—CH$_2$—CH$_2$), 2.55 (t; 2H; —CH$_2$—CH$_2$—C=O). |
| $^{13}$C NMR : | (CD$_3$OD) |

-continued

| δ (ppm) : | 10.60 (d), 26.60 (d), 38.05 (s), 41.25 (s), 58.15 (s), 59.22 (s), 162.20 (d), 174.72 (s). |

Synthesis of N-[3-chloro-2-(hydroxyimino)-3-methylbutyl]-2-nitroimidazole (Compound IX)

2-Nitroimidazole (2 g, 17.7 mmol) was added to a solution of sodium hydroxide (0.76 g, 19 mmol) in water (20 ml) . The solution was stirred for ca 1 h. at RT, the water was removed under reduced pressure and the residue dried in vacuo for at least ca 3 h.

To the sodium salt of 2-nitroimidazole prepared above was added acetonitrile (50 ml), 15-crown-5-ether (3.5 ml, 14.3 mmol) and 4-bromo-2-methyl-2-butene (2 ml; 17.4 mmol). The mixture was stirred at RT for ca 16 h. and then the solvent was removed to leave a crude semi-solid which was purified by column chromatography on silica. The intermediate product, 1-(3-methyl-2-butenyl)-2-nitroimidazole (80% yield) was eluted using a mixture of petroleum ether (40–60)/ethyl acetate (ratio 4:1 respectively).

The N-alkylated product of first step (1.0 g, 5.5 mmol) was dissolved in iso-amyl nitrite (1.0 ml, 7.4 mmol) at RT and then cooled in an ice bath (outside temp. measured −8° C.). Concentrated hydrochloric acid (0.9 ml, 36% HCl) was added dropwise while stirring. The reaction was stirred for ca 15 min. before storing overnight at −20° C.

Glacial acetic acid (10 ml) was added and the mixture was kept at −20° C. for ca 30–35 min. Methanol (10 ml, cold) was added and the reaction mixture was stored at −15° C. for ca 3 h., whence a white precipitate formed. The product was filtered very quickly, washed with ice-cold methanol (5 ml.) and then dried in vacuo, yielding Compound IX as a white powder.
Analysis:

| $^1$H NMR : | (CD$_3$CN) |
| δ (ppm) : | 1.80 (s; 6H; —CH$_3$), 5.43 (s; 2H; N=C—CH$_2$—N), 7.05 (s; 1H; $^4$H), 7.20 (s; 1H; $^5$H), 9.63 (s; 1H; N—OH). |
| $^{13}$C NMR : | (DMSO—d$_6$) |
| δ (ppm) : | 30.02 (s), 42.38 (s), 70.66 (s), 126.41 (s), 127.53 (s), 153.25 (s). |

Synthesis of N-[4,8-diaza-2,10-bis(hydroxyimino)-7-oxo-3,3,9,9-tetramethyl-undecyl]-2-nitroimidazole (Compound X)

A solution of 1-(2-nitro-1-imidazola)-3-chloro-3-methylbutan-2-one-2-monoxime (90 mg; 0.36 mmol) in a mixture of dry acetonitrile (5 ml) and absolute ethanol (5 ml) was added to a slurry of 7-amino-4-aza-3,3-dimethylheptan-2,5-dione-2-monoxime (61 mg; 0.36 mmol) and sodium bicarbonate (137 mg; 1.65 mmol) in dry acetonitrile (10 ml), over a period of ca 10⁻. The reaction mixture was stirred for ca 18 h., and then the solvent was removed under reduced pressure. The residue was redissolved in 50:50 H$_2$O/MeCN (10 ml), prior to purification by preparative HPLC. The desired fractions were collected, bulked together and the solvent removed under reduced pressure to yield Compound X as a yellow glassy solid, (40 mg; 31%).
HPLC Purification
Column: C$_{18}$-PRP-1 (Preparative Reverse Phase)
Solvents: A=H$_2$O B=MeCN-System: Gradient
Flow Rate: 2.5 ml/min.
U.V detector: λ=210 nm Gradient Profile:

| Time | % B |
|---|---|
| 0 | 0 |
| 5 | 0 |
| 15 | 80 |
| 20 | 80 |
| 22 | 0 |
| 25 | 0 |

Retention time of product: 15.0 min.
Analysis:

| $^1$H NMR : | (CD$_3$OD) |
| δ (ppm) : | 1.28 (s; 6H; —CH$_3$), 1.40 (s; 6H; —CH$_3$), 1.75 (s; 3H; —CH$_3$—C=N—O), 2.20 (t; 2H; CH$_2$—CH$_2$—N), 2.52 (t; 2H; O=C—CH$_2$—CH$_2$), 5.45 (s; 2H; O—N=C—CH$_2$—N), 7.05 (s; 1H; $^4$H), 7.35 (s; 1H; $^5$H |
| $^{13}$C NMR : | (CD$_3$OD) |
| δ (ppm) : | 10.60 (s), 26.76 (s), 40.84 (s), 43.06 (s), 58.18 (s), 59.10 (s), 128.36 (s), 128.85 (s), 148.50 (s), 157.90 (s), 162.17 (s), 174.52 (s). |

Synthesis of Methyl Pyruvate Oxime (Compound XI)

To a stirred solution of hydroxylamine hydrochloride (14 g; 0.2 mol) in water (20 ml) was added methyl pyruvate (21 g; 0.2 mol) and methanol (130 ml). The reaction mixture was stirred in the dark for ca 18 h. After removal of the methanol solvent under reduced pressure, the pH of the remaining aqueous solution was adjusted to pH7, saturated with sodium chloride and the product extracted into dichloromethane (3×50 ml). The separated dichloromethane fractions were bulked together, dried over magnesium sulphate and filtered off in air. Removal of the solvent under reduced pressure gave a white solid which was recrystallised from water to yield Compound XI as clear needles, (14.71 g; 62%).
Analysis:

| m.p : | 69–71° C. |
| $^1$H NMR : | (CDCl$_3$) |
| δ (ppm) : | 2.10 (s; 3H; —CH$_3$), 3.85 (s; 3H; —O—CH$_3$), 9.35 (br,s; 1H; N—OH) |
| $^{13}$C NMR : | (CDCl$_3$) |
| δ (ppm) : | 10.51 (s), 52.74 (s), 149.64 (s), 164.12 (s) |

Synthesis of 4,8-diaza-undecan-2,3,9,10-tetra-one-2,10-bis oxime (Compound XII)

A solution of Compound XI (1.66 g; 14 mmol) in methanol (10 ml) was added dropwise to a stirred solution of propylenediamine (0.5 g; 6.8 mmol) in methanol (8 ml), over a period of ca 30 minutes. After the addition was complete, the reaction mixture was heated under reflux for ca 72 h., whence the solution became deep orange in colour. After cooling, the solvent was removed under reduced pressure, yielding a deep orange oil which was redissolved in acetonitrile and stirred at RT. Almost immediately a cream precipitate appeared in the solution which was isolated by filtration in air and dried in vacuo. Recrystallisation of the solid from hot water yielded Compound XII as a pale cream powder, (1.15 g; 71%).

Analysis:

| | |
|---|---|
| m.p. : | 185–188° C. |
| $^1$H NMR : | (DMSO-d$_6$) |
| δ (ppm) : | 1.55 (m; 2H; —CH$_2$—<u>CH$_2$</u>—CH$_2$), 1.85 (s; 6H; —CH$_3$—C=N—O), 3.12 (m; 4H; N—<u>CH$_2$</u>—CH$_2$), 8.00 (t; 2H; N—OH). |
| $^{13}$C NMR : | (DMSO—d$_6$) |
| δ (ppm) : | 9.60 (s), 29.30 (s), 35.81 (s), 150.3 (s), 163.7 (s). |

Synthesis of N,N'-bis-[2-(hydroxyimino)-1,1-dimethylpropy]-1,3-propandiamide (Compound XIII)

A mixture of malonic acid (0.26 g, 2.5 mmol) and pyridine (0.4 ml) in acetonitrile (20 ml) was added to a stirred solution of di-N-succinimidyl carbonate in acetonitrile (20 ml), maintained under a dry dinitrogen atmosphere. The reaction mixture was stirred for ca 4 h., until evolution of the carbon dioxide gas generated by the reaction had ceased, and then a solution of the 3-amino-3-methylbutan-2-one-2-monoxime (0.58 g; 5 mmol) in acetonitrile (10 ml) was added. After ca 5 minutes a white solid began to form in the solution and stirring continued for ca 18 h. to ensure complete precipitation of the product.

The solid was filtered off in air, washed with aliquots of acetonitrile (3×10 ml) and dried in vacuo to yield Compound XIII, (240 mg; 32%).
Analysis:

| | |
|---|---|
| m.p. : | 165–168° C. |
| $^1$H NMR : | 1.22 (s; 12H; —CH$_3$), 1.60 (s; 3H; —CH$_3$—C=N—O), 1.75 (s; 3H; —CH$_3$—C=N—O), 2.80 (s; 2H; O=C—CH$_2$—C=O). |

Synthesis of 11-(tBoc amino)-4,8-diaza-3,3-dimethylundecan-2-one monoxime (Compound XIV)

A solution of 3-chloro-3-methyl-2-nitrosobutane (0.64 g; 4.6 mmol) in acetonitrile (30 ml) was added dropwise to a stirred mixture of N-tBoc-dipropylenetriamine (0.5 g; 2.3 mmol) and sodium bicarbonate (0.6 g; 7.1 mmol) in acetonitrile (40 ml). The reaction mixture was stirred for ca 18 h., then the solvent was removed under reduced pressure to yield an oil. The crude product was dissolved in water, the solution saturated with sodium chloride, and the product extracted into dichloromethane (3×30 ml). The organic fractions were separated, bulked together and dried over magnesium sulphate. After filtration, removal of the solvent under reduced pressure yielded a clear oil. The oil was slurried with diethylether (30 ml), the ether was decanted off and the product was dried in vacuo. Crystallisation of a solution of the product in dichloromethane\40–60 petrol ether at −4° C. yielded Compound XIV as a white powder, (0.45 g; 59%).
Analysis:

| | |
|---|---|
| $^1$H NMR : | (CD$_3$CN) |
| δ (ppm) : | 1.25 (s; 6H; —CH$_3$), 1.40 (s; 9H; —C(CH$_3$)$_3$), 1.70 (m; 2H; —CH$_2$—<u>CH$_2$</u>—CH$_2$), 1.80 (s; 3H; —CH$_3$—C=N—O), 1.90 (m; 2H; —CH$_2$—<u>CH$_2$</u>—CH$_2$), 2.85 (t; 2H; CH$_2$—<u>CH$_2$</u>—N), 2.95 (t; 2H; —CH$_2$—<u>CH$_2$</u>—N), 3.18 (t; 2H; —CH$_2$—<u>CH$_2$</u>—N), 3.26 (m; 2H; —CH$_2$—<u>CH$_2$</u>—N), 5.34 (br,s; 1H; —NH). |

Technetium Labelling

Preparation of Technetium Complex of Compound I 0.1 ml of compound I solution (10 mg/ml in 0.9% aq NaCl) plus 1 ml 1 M aq NaHCO$_3$ plus 1 GBq $^{99m}$TcO$_4^-$ (1 ml generator eluate) were mixed in a sealed vial containing approximately 10 mg tin metal together with 1 ml stannous tartrate solution (0.1 mg/ml in water). After standing at room temperature for 6 hours >80% Tc complex had formed as judged by TLC and HPLC (t$_R$=5.6 min).

Preparation of Technetium Complex of Compound VII 0.1 ml of compound VII solution (10 mg/ml in 0.9% aq NaCl) plus 1 ml 1M aq NaHCO$_3$ plus 1 GBq $^{99m}$TcO$_4^-$ (1 ml generator eluate) were mixed in a sealed vial together with 1 ml stannous tartrate solution (0.1 mg/ml in water). After 1 hour standing at room temperature analysis by HPLC and TLC indicated >80% Tc complex (HPLC t$_R$=6.9 minutes).

Preparation of Technetium Complex of Compound VIII 0.14 ml compound VIII solution (prepared by dissolving 1.7 mg ligand in 200 μl ethanol mixed with 70 μl 0.9% aq NaCl plus 1 ml 1M aq NaHCO$_3$ plus 1 GBq $^{99m}$TcO$_4^-$ (1 ml generator eluate) were mixed in a sealed vial together with 1 ml stannous tartrate solution (0.1 mg/ml in water). After standing at room temperature for 1 hour analysis by HPLC and TLC indicated >90% Tc complex (HPLC t$_R$=8.2 minutes).

Preparation of Technetium Complex of Compound X 0.1 ml of compound X solution (10 mg/ml in 0.9% aq. NaCl) plus 1 ml 1M aq NaHCO$_3$ plus 1 GBq TcO$_4^-$ (1 ml generator eluate) were mixed in a sealed vial containing approximately 10 mg tin metal together with 1 ml stannous tartrate solutions (0.1 mg/ml in water). After standing at room temperature for 1 hour analysis by HPLC and TLC indicated >40% Tc complex (HPLC t$_R$=9.4 minutes) which could be increased to >80% by preparative HPLC.

Preparation of Technetium Complex of Compound XII 0.22 ml of compound XII solution (2.7 mg in 0.27 ml 0.9% saline plus 0.3 ml EtOH) plus 0.1 ml 1 M aq NaHCO$_3$ plus 1 GBq $^{99m}$TcO$_4^-$ (1 ml generator eluate) were mixed in a sealed vial containing approximately 10 mg tin metal together with 1 ml stannous tartrate solution (0.1 mg/ml in water). After standing at room temperature for 6 hours TLC and HPLC analysis indicated >80% Tc complex (HPLC t$_R$=5.0 minutes).

Analytical Methods

Thin Layer Chromatography:

Whatman No. 1 paper eluted with 50% aq acetonitrile.

Reduced hydrolysed Tc R$_f$ 0.0.

ITLC SG eluted with 0.9% aq.aCl.

free pertechnetate=R$_f$ 1.0.

% complex=100-free pertechnetate-reduced hydrolysed Tc.

HPLC:

Hamilton PRP-1 column eluted at 2 ml/min gradient 100% pH 7.5 10 mM sodium phosphate to 100% tetrahydrofuran over 17 minutes Hypoxia Model Chinese hamster V79 379A fibroblasts in suspension in vitro were used as the test system, gassed with air/5% CO$_2$ (oxic) or nitrogen/5% CO$_2$ (hypoxic). This is a test system very widely used in assessing hypoxia-induced binding or bioreductive drugs. Tc-99m labelled compounds were added at concentrations which are likely to be clinically achievable (up to about 50 μmol dm$^{-3}$).

V79 379A Chinese hamster cells were harvested from exponential suspension culture and resuspended at 1.1×10$^6$ cells cm$^{-3}$ in Eagle's minimum essential medium with 7.5% foetal calf serum. Cells (20 cm$^3$) were transferred to small spinner vessels and gassed with either air/5% (oxic) or nitrogen/5% CO$_2$ (hypoxic) at 37° C. After 30 minutes, between 0.5 cm³ and 1 cm³ of Tc-99m labelled compound was added. At timed intervals, 1 cm³ of cell suspension was withdrawn from each flask and chilled on ice in small polystyrene centrifuge tubes. The cells were centrifuged and washed three times in ice-cold medium (Eagle's minimum essential medium) to give constant counts in the cell pellet. The pellets were counted in an LKB 1282 Compugamma counter. The initial supernatant was diluted 1 in 100 with saline and 1 cm³ was counted. All samples were counted at the end of the incubation period and counts have been corrected for decay during counting but not for decay during incubation.

Attempts were made to decrease the amount of non-specific binding by incubating the cell samples in a large volume of medium for one hour at 37° C. under oxic conditions. Although this treatment reduced the total counts in both hypoxic and oxic cell pellets, it did not improve the differential.

Results

Figure 1:
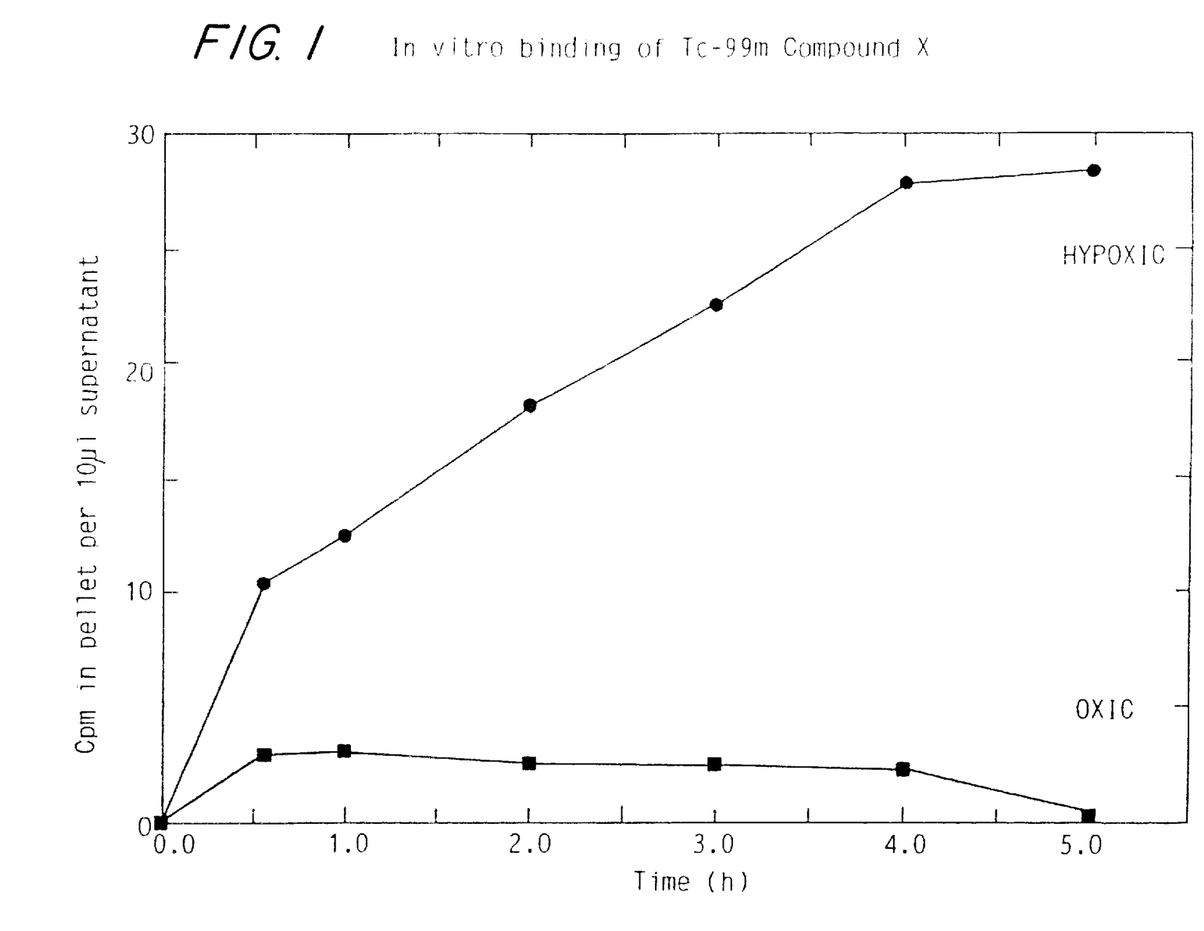
Figure 2:
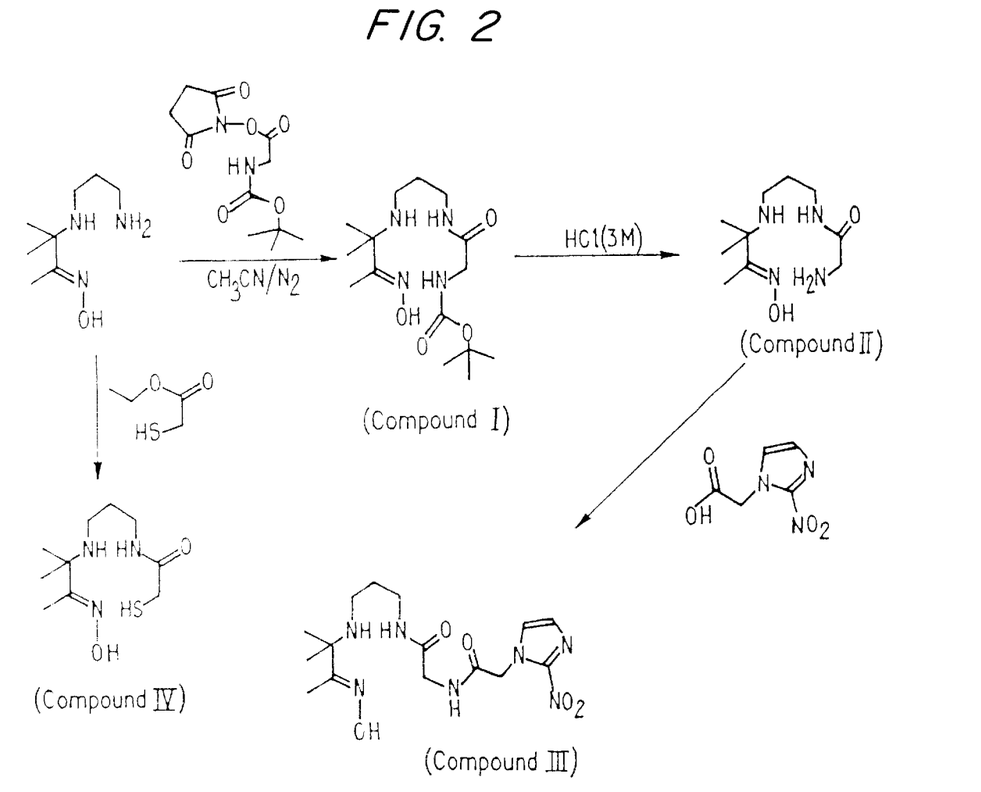
Figure 3:
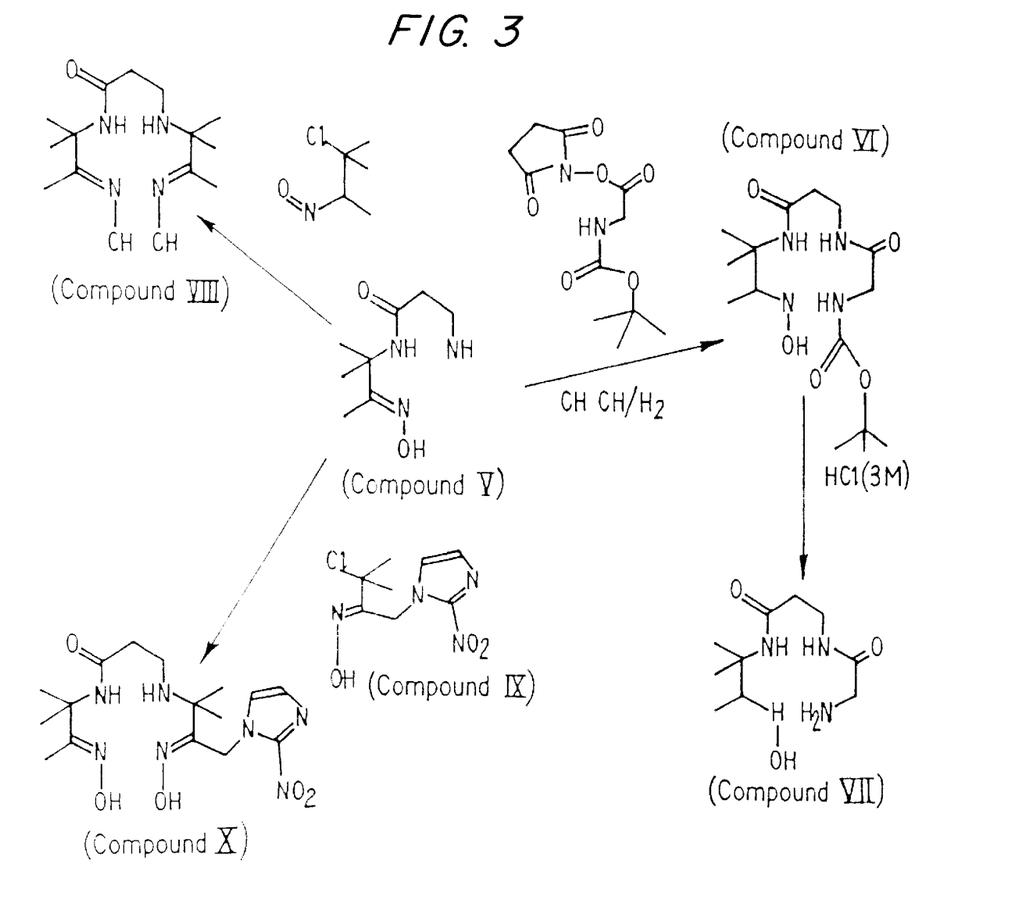
Figure 4:
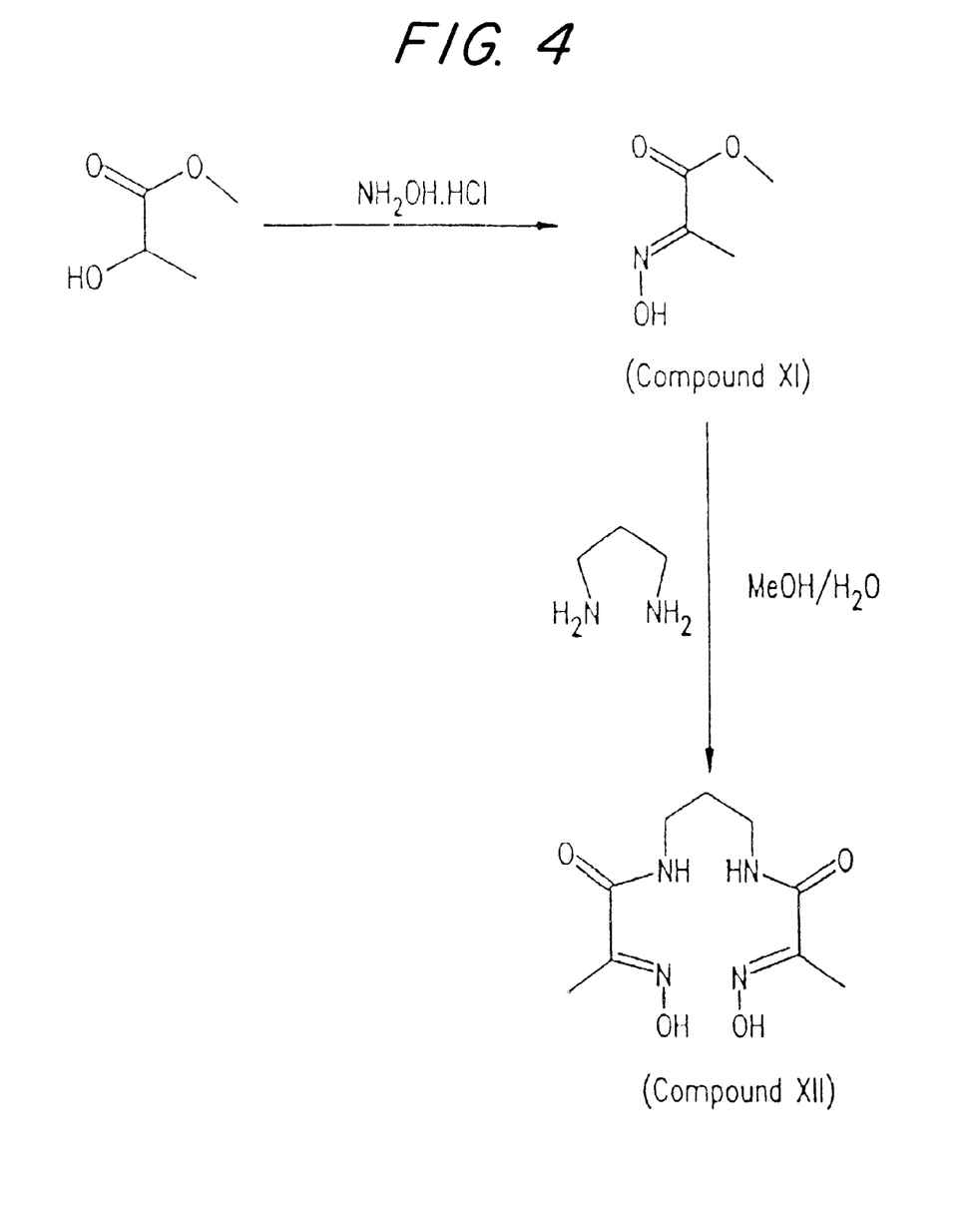
Figure 5:
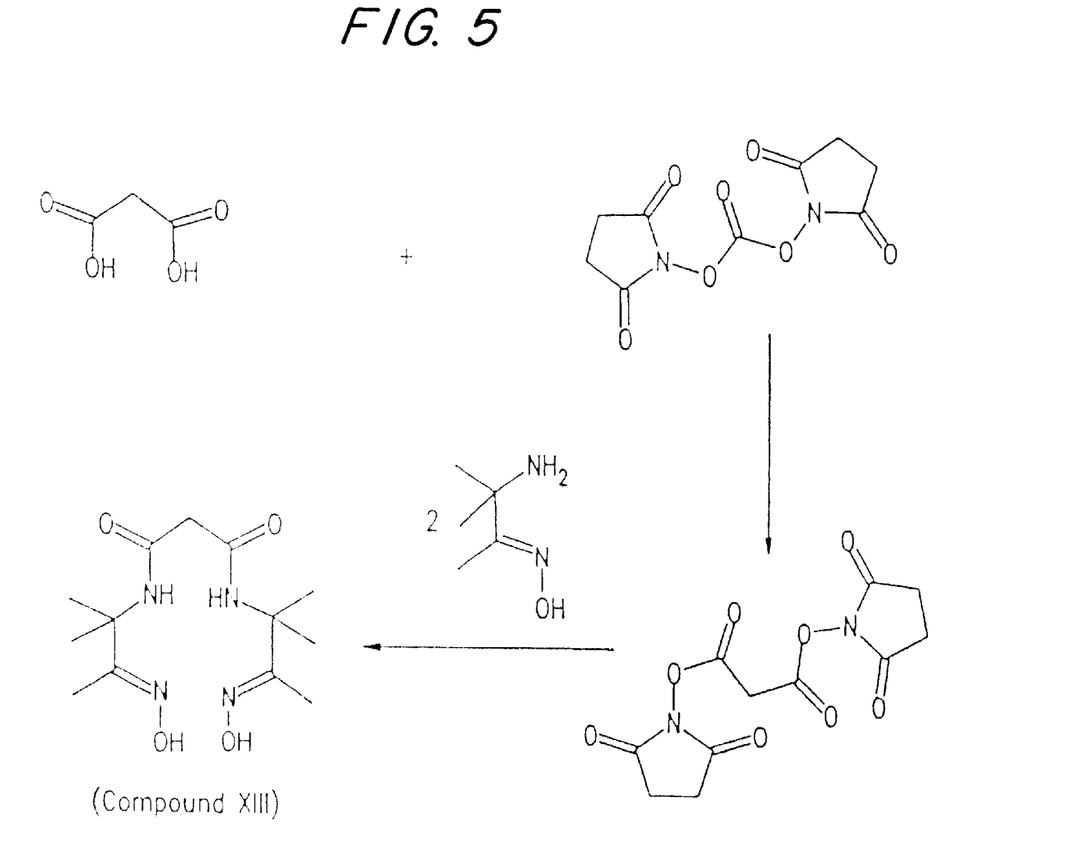
Figure 6:
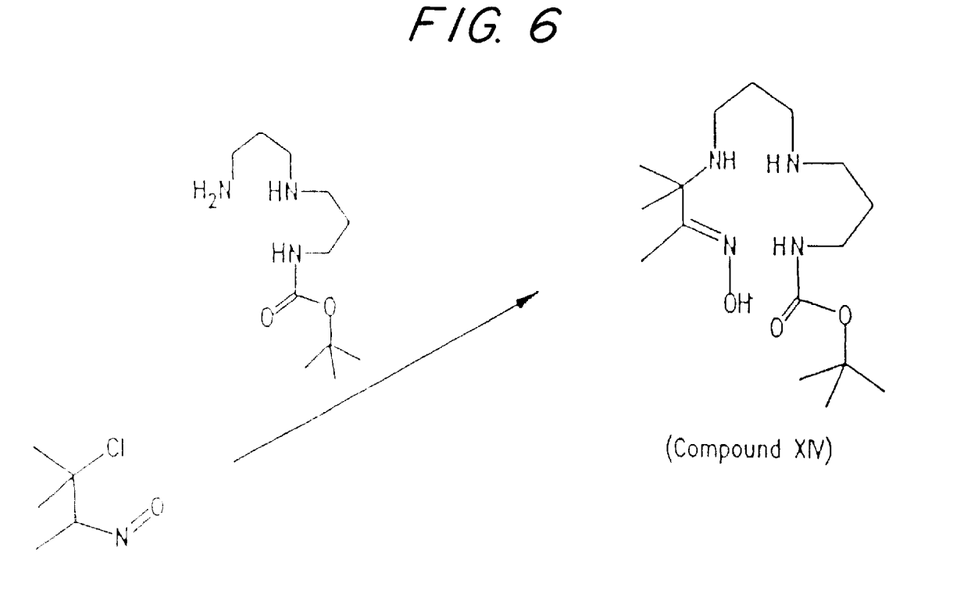

FIG. 1 shows the hypoxic/oxic cell uptake of $^{99m}$Tc-labelled compound X in the above in vitro model.

In vitro binding of $^{99m}$Tc compound X to V79 cells

| Time/h | cpm in pellet (x 10⁵) | | cpm/ml in supernatant (x 10⁷) | | Ratio hypoxic/oxic |
|---|---|---|---|---|---|
| | oxic | hypoxic | oxic | hypoxic | oxic |
| 0.55 | 4.02 | 15.00 | 1.37 | 1.44 | 3.55 |
| 1 | 4.13 | 18.30 | 1.36 | 1.45 | 4.16 |
| 2 | 3.50 | 26.80 | 1.39 | 1.47 | 7.18 |
| 3 | 3.5 | 33.00 | 1.39 | 1.46 | 8.98 |
| 4 | 3.21 | 40.60 | — | 1.46 | 12.04 |
| 5 | 2.89 | 43.60 | 1.48 | 1.54 | 14.50 |

Excluded from the scope of the following claims are compounds having the following formula, and technetium complexes of the compounds:

where X is H or C1–C6 alkyl or hydroxyalkyl, and either

$X^1Y$ is hydrogen, or $X^1$ is C1–20 alkylene or hydroxyalkylene, and

Y is a targeting group and/or protein reactive functionality.

We claim:

1. A radiometal complex comprising a metal chelating compound and a radiometal, where the metal chelating compound has the formula wherein the groups R are the same or different and each is selected form the group consisting of H, $C_{1-20}$ alkyl, alkoxy, alkoxyalkyl, primary, secondary or tertiary amide, primary, secondary or tertiary amine, carboxylic acid, hydroxyalkyl and aryl, or 1 to 3 of the $CR_2$ groups adjacent and N atom represents a CO moiety, or two Rs of any $CR_2$ group or of two or more separate $CR_2$ groups are combined to form a C3–C6 cycloalkyl, aryl, spiropiperidinyl or other heterocyclic ring, provided that at least one $CR_2$ group adjacent an N atom represents a CO moiety, provided that one to three Rs each optionally comprises a targeting group or a protein reactive functionality, and provided that the following compounds are excluded where X is selected from the group consisting of H, C1–C6 alkyl and hydroxyalkyl, and either $X^1Y$ is hydrogen, or

$X^1$ is $C_{1-20}$ alkylene or hydroxyalkylene, and

Y is a targeting group, a protein reactive functionality, or both.

2. The radiometal complex as claimed in claim 1 which is neutral.

3. The radiometal complex as claimed in claim 1, wherein the radiometal is selected from $^{99m}$Tc, $^{186}$Re, $^{188}$Re, $^{67}$Cu and $^{107}$Ag.

4. A metal chelating compound of the formula wherein the groups R are the same or different and each is selected form the group consisting of H, C1–20 alkyl, alkoxy, alkoxyalkyl, primary, secondary, or tertiary amide, primary, secondary or tertiary amine, carboxylic acid, hydroxyalkyl and aryl, or 1 to 3 of the CR2 groups adjacent an N atom represents a CO moiety, or two Rs of any CR2 group or of two or more separate CR2 groups are combined to form a C3–C6 cycloalkyl, aryl, spiropiperidinyl or other heterocyclic ring, provided that at least one CR2 group adjacent an N atom represents a CO moiety, provided that one to three Rs each comprise a targeting group or a protein reactive functionality, and provided that the following compounds are excluded where
X is H, C1–C6 alkyl and hydroxyalkyl, and either
$X^1Y$ is hydrogen, or
$X^1$ is C1–C20 alkylene or hydroxyalkylene, and
Y is a targeting group, a protein reactive functionality, or both.

5. The radiometal complex according to claim 1, in which one or two Rs comprise a targeting group or a protein reactive functionality, and 1 to 3 of the $CR_2$ groups adjacent an N atom represent a CO moiety, and each remaining R contains 0–6 carbon atoms.

6. The radiometal complex according to claim 5, in which each remaining R is H or methyl.

7. The radiometal complex according to claim 1, having the formula Q-A-L or $(Q-A)_2$-L wherein Q is a targeting group or a protein reactive functionality, A is a linking group, and L is the metal-chelating compound.

8. The radiometal complex according to claim 1, wherein the targeting group is a bioreductive group.

9. The radiometal complex according to claim 8, wherein the bioreductive group is a nitroimidazole or substituted analog thereof.

10. A compound of structure

* * * * *